(12) United States Patent
Kuzmanich et al.

(10) Patent No.: US 9,890,094 B2
(45) Date of Patent: Feb. 13, 2018

(54) HIGH MESO-SURFACE AREA AND HIGH ACID SITE DENSITY PENTASIL ZEOLITE FOR USE IN XYLENE CONVERSION

(71) Applicant: UOP LLC, Des Plaines, IL (US)

(72) Inventors: Gregory B. Kuzmanich, Evanston, IL (US); Jaime G. Moscoso, Mount Prospect, IL (US); Deng-Yang Jan, Elk Grove Village, IL (US)

(73) Assignee: UOP LLC, Des Plaines, IL (US)

( * ) Notice: Subject to any disclaimer, the term of this patent is extended or adjusted under 35 U.S.C. 154(b) by 109 days.

(21) Appl. No.: 14/636,624

(22) Filed: Mar. 3, 2015

(65) Prior Publication Data

US 2016/0257632 A1    Sep. 8, 2016

(51) Int. Cl.
*C07C 7/12* (2006.01)
*B01J 29/40* (2006.01)
*C07C 5/27* (2006.01)
*C07C 7/00* (2006.01)
*C01B 39/36* (2006.01)
*B01J 35/00* (2006.01)
*B01J 35/02* (2006.01)
*B01J 35/10* (2006.01)

(52) U.S. Cl.
CPC ............. *C07C 5/2737* (2013.01); *B01J 29/40* (2013.01); *B01J 35/002* (2013.01); *B01J 35/023* (2013.01); *B01J 35/026* (2013.01); *B01J 35/1057* (2013.01); *B01J 35/1061* (2013.01); *C01B 39/36* (2013.01); *C07C 5/2708* (2013.01); *C07C 5/2775* (2013.01); *C07C 7/005* (2013.01); *C07C 7/12* (2013.01); *B01J 2229/186* (2013.01); *B01J 2229/42* (2013.01); *C07C 2529/40* (2013.01); *C07C 2529/70* (2013.01); *Y02P 20/52* (2015.11)

(58) Field of Classification Search
CPC ....... C07C 5/2737; C07C 5/2775; C07C 7/12; C07C 7/005; C01B 39/36; C01B 39/365; C01B 39/38; C01B 39/40; C01B 39/48
See application file for complete search history.

(56) References Cited

U.S. PATENT DOCUMENTS

| | | | |
|---|---|---|---|
| 3,996,305 A | 12/1976 | Berger | |
| 4,341,914 A | 7/1982 | Berger | |
| 4,381,419 A * | 4/1983 | Wylie | C07C 7/11 203/99 |
| 4,642,406 A | 2/1987 | Schmidt | |
| 4,939,110 A | 7/1990 | Sachtler | |
| 5,157,183 A | 10/1992 | Cotterman | |
| 5,417,844 A | 5/1995 | Boitiaux | |
| 5,981,817 A | 11/1999 | Kao | |
| 6,180,550 B1 | 1/2001 | Beck | |
| 6,303,839 B1 | 10/2001 | Marker | |
| 6,355,853 B1 | 3/2002 | Sharma | |
| 6,413,941 B1 | 7/2002 | Garnett et al. | |
| 6,858,129 B2 | 2/2005 | Mohr | |
| 7,317,133 B2 | 1/2008 | Vora | |
| 7,425,660 B2 | 9/2008 | Larson | |
| 7,939,701 B2 | 5/2011 | Whitchurch | |
| 8,030,239 B2 | 10/2011 | Oh | |
| 8,134,037 B2 | 3/2012 | Bogdan | |
| 8,273,935 B2 | 9/2012 | Rekoske | |
| 8,574,542 B2 | 11/2013 | Domokos | |
| 8,609,921 B1 * | 12/2013 | Nicholas | C01B 39/48 585/475 |
| 8,692,044 B2 | 4/2014 | Ou | |
| 8,697,929 B2 | 4/2014 | Ou | |
| 8,747,807 B2 * | 6/2014 | Jan | C01B 39/48 208/135 |
| 8,889,937 B2 | 11/2014 | Haizmann | |
| 8,889,940 B2 | 11/2014 | Bogdan | |
| 8,900,548 B2 * | 12/2014 | Burton | B01J 29/70 423/706 |
| 9,415,381 B2 * | 8/2016 | Burton | B01J 29/70 |
| 2007/0060778 A1 | 3/2007 | Bogdan | |
| 2008/0146859 A1 | 6/2008 | Rekoske | |
| 2011/0245566 A1 * | 10/2011 | Bogdan | C07C 5/2737 585/481 |
| 2012/0004485 A1 * | 1/2012 | Jan | C01B 39/48 585/457 |

FOREIGN PATENT DOCUMENTS

WO    035626 A1    3/2014
WO    150875 A1    9/2014

OTHER PUBLICATIONS

U.S. Appl. No. 14/636,541, filed Mar. 3, 2015, Kuzmanich.
U.S. Appl. No. 14/636,798, filed Mar. 3, 2015, Schoenfeldt.
U.S. Appl. No. 14/636,672, filed Mar. 3, 2015, Moscoso.
U.S. Appl. No. 14/636,898, filed Mar. 3, 2015, Moscoso.
U.S. Appl. No. 14/636,718, filed Mar. 3, 2015, Jan.
Raj, "Selective Formation of 1,2,4 Isomer among Trimethylbenzenes in the Methylation of Xylenes over Al- Ga-, and Fe-Silicates with MEL Structure" Journal of Catalysis, V. 138, pp. 518-524, Dec. 1992, ISSN 0021-9517, Academic Press.

(Continued)

*Primary Examiner* — Brian McCaig
*Assistant Examiner* — Jason Chong

(57) ABSTRACT

A process for the production of para-xylene is presented. The process includes the isomerization of C8 aromatics to para-xylene utilizing a new catalyst. The new catalyst and designated as UZM-54 is represented by the empirical composition in the as synthesized and anhydrous basis expressed by the empirical formula of:

$$M_m^{n+}R_{1\ r1}^{p1+}R_{2\ r2}^{p2+}Al_{1-x}E_xSi_yO_z$$

where M is an alkali, alkaline earth, or rare earth metal such as sodium and/or potassium, $R_1$ and $R_2$ are organoammonium cation and E is a framework element such as gallium, iron, boron, or indium. UZM-54 are characterized by unique x-ray diffraction patterns, high meso surface area, low Si/Al ratios.

22 Claims, No Drawings

(56) References Cited

OTHER PUBLICATIONS

Reddy, "Synthesis, Characterization, and Catalytic Properties of Metallo-Titanium Silicate Molecular Sieves with MEL Topology" Journal of Catalysis, 145, 1994, pp. 73-78.

Raj, "Catalytic Properties of [Al], [Ga], and [Fe]-silicate Analogs of ZSM-11 in C7 and C8 Aromatic Hydrocarbon Reactions: Influence of Isomorphous Substitution" Proc. Int. Zeolite Conf., 9th, 1993, 2, pp. 551-558.

Ahn, "Tailoring Mesoscopically Structured H-ZSM5 Zeolites for Toluene Methylation" Journal of Catalysis, 2014, pp. 271-280.

John, "Zeolite Containing Catalysts for the Conversion of C8-aromatics Fractions" Catalysis Today, 49, 1999 Elsevier Science B.V., pp. 211-220.

Harrison, "Some Sorptive and Catalytic Properties of Zeolite Nu-10" Zeolites, Jan. 1987, vol. 7, pp. 28-34.

\* cited by examiner

HIGH MESO-SURFACE AREA AND HIGH ACID SITE DENSITY PENTASIL ZEOLITE FOR USE IN XYLENE CONVERSION

FIELD OF THE INVENTION

The present invention relates to the use of a new family of aluminosilicate zeolites, having a designation of UZM-54. UZM-54 is characterized by unique x-ray diffraction patterns, high meso-surface area and low Si/Al ratio compositions.

BACKGROUND

Most new aromatics complexes are designed to maximize the yield of benzene and para-xylene. Benzene is a versatile petrochemical building block used in many different products based on its derivation including ethylbenzene, cumene, and cyclohexane. Para-xylene is also an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the Handbook of Petroleum Refining Processes, 2d. Edition in 1997 by McGraw-Hill.

U.S. Pat. No. 3,996,305 to Berger discloses a fractionation scheme primarily directed to trans alkylation of toluene and $C_9$ alkylaromatics in order to produce benzene and xylene. The trans alkylation process is also combined with an aromatics extraction process. The fractionation scheme includes a single column with two streams entering and with three streams exiting the column for integrated economic benefits.

U.S. Pat. No. 4,341,914 to Berger discloses a transalkylation process with recycle of $C_9$ alkylaromatics in order to increase yield of xylenes from the process. The transalkylation process is also preferably integrated with a paraxylene separation zone and a xylene isomerization zone operated as a continuous loop receiving mixed xylenes from the transalkylation zone feedstock and effluent fractionation zones.

U.S. Pat. No. 4,642,406 to Schmidt discloses a high severity process for xylene production that employs a transalkylation zone that simultaneously performs as an isomerization zone over a nonmetal catalyst. High quality benzene is produced along with a mixture of xylenes, which allows para-xylene to be separated by absorptive separation from the mixture with the isomer-depleted stream being passed back to the trans alkylation zone.

U.S. Pat. No. 5,417,844 to Boitiaux et al. discloses a process for the selective dehydrogenation of olefins in steam cracking petrol in the presence of a nickel catalyst and is characterized in that prior to the use of the catalyst, a sulfur-containing organic compound is incorporated into the catalyst outside of the reactor prior to use.

The importance of para-xylene production has led to the development of many different processes. However, there are losses associated with these processes. Improvements to reduce and minimize losses are important for the economics of para-xylene production.

SUMMARY

A first embodiment of the invention is a process for the production of para-xylene, comprising passing a mixture of hydrocarbons comprising xylenes to an isomerization reactor, operated at isomerization reaction conditions, to form a reaction mixture over an isomerization catalyst, and to generate an effluent stream comprising p-xylene; wherein the isomerization catalyst is UZM-54. For the purposed of this application, recited intensity symbols are defined as w=0-15; m=15-60; s=60-80 and vs=80-100.

The UZM-54 aluminosilicate zeolite is a microporous crystalline structure comprising a framework of $AlO_2$ and $SiO_2$ tetrahedral units, and an empirical composition in the as synthesized and anhydrous basis expressed by the empirical formula of $M_m^{n+}R_{1\ r1}^{p_1+}R_{2\ r2}^{p_2+}AlSi_yO_z$ where M is at least one exchangeable cation selected from the group consisting of alkali and alkaline earth metals, "m" is the mole ratio of M to Al and varies from about 0 to about 1, $R_1$ is at least one organoammonium cation selected from the group consisting of quaternary ammonium cations, diquaternary ammonium cations, "$r_1$" is the mole ratio of $R_1$ to Al and has a value of about 0.1 to about 3.0, $R_2$ is at least one organoammonium cation selected from the group consisting of protonated alkanolamines, protonated amines, protonated diamines, and quaternized alkanolammonium cations, "$r_2$" is the mole ratio of $R_2$ to Al and has a value of about 0 to about 3.0, "n" is the weight average valence of M and has a value of about 1 to about 2, "$p_1$" is the weighted average valence of $R_1$ and has a value of about 1 to about 2, "$p_2$" is the weighted average valence of $R_2$ and has a value of about 1 to about 2, "y" is the mole ratio of Si to Al and varies from greater than 11 to about 30 and "z" is the mole ratio of O to Al and has a value determined by the equation $z=(m \cdot n + r_1 \cdot p_1 + r_2 \cdot p_2 + 3 + 4 \cdot y)/2$ and it is characterized in that it has the x-ray diffraction pattern having at least the d spacing and intensities set forth in the following Table:

TABLE

| 2Θ | d(Å) | I/Io |
|---|---|---|
| 7.91-8.05 | 10.83-11.16 | vs |
| 8.84-9.01 | 9.80-9.99 | vs |
| 14.87-14.91 | 5.93-5.95 | w-m |
| 15.51-15.65 | 5.65-5.70 | w |
| 15.91-16.12 | 5.49-5.56 | w |
| 20.41-20.59 | 4.31-4.34 | w |
| 20.82-20.94 | 4.25-4.43 | w |
| 23.25-23.61 | 3.76-3.82 | vs |
| 23.84-23.92 | 3.71-3.72 | m |
| 24.35-24.75 | 3.59-3.65 | m |
| 26.80-26.95 | 3.30-3.32 | w |
| 29.33-29.46 | 3.02-3.04 | w |
| 30.01-30.13 | 2.96-2.97 | w |
| 30.32-30.32 | 2.94-2.94 | w |

An embodiment of the invention is one, any or all of prior embodiments in this paragraph up through the first embodiment in this paragraph wherein the isomerization reaction conditions include a temperature between 190° C. and 350° C. An embodiment of the invention is one, any or all of prior embodiments in this paragraph up through the first embodiment in this paragraph wherein the isomerization reaction conditions include a temperature between 220° C. and 270° C. An embodiment of the invention is one, any or all of prior embodiments in this paragraph up through the first embodiment in this paragraph wherein the isomerization reaction conditions include a pressure sufficient to maintain the reaction mixture in the liquid phase. An embodiment of the invention is one, any or all of prior embodiments in this paragraph up through the first embodiment in this paragraph wherein the pressure is at least 1025 kPa. An embodiment of the invention is one, any or all of prior embodiments in this paragraph up through the first embodiment in this paragraph wherein the mixture of hydrocarbons further includes ethylbenzene. An embodiment of the invention is one, any or all of prior embodiments in this paragraph up through the first embodiment in this paragraph where M in the zeolite is selected from the group consisting of lithium, sodium, potassium, cesium, strontium, calcium, barium and mixtures thereof. An embodiment of the invention is one, any or all of prior embodiments in this paragraph up through the first embodiment in this paragraph where M in the zeolite is a mixture of an alkali metal and an alkaline earth metal. An embodiment of the invention is one, any or all of prior embodiments in this paragraph up through the first embodiment in this paragraph where $R_1$ in the zeolite is selected from the group consisting of dimethyldipropylammonimum, diethyldipropylammonium, propyltrimethylammonium, hexamethonium, and mixtures thereof. An embodiment of the invention is one, any or all of prior embodiments in this paragraph up through the first embodiment in this paragraph where $R_2$ in the zeolite is selected from the group consisting of diethanolamine, N-methylethanolamine, 2-dimethylaminoethanol, N-methyldiethanolamine, 2-diethylamino ethanol, 2-isopropylamino ethanol, 2-diisopropylamino ethanol, 3-dimethylamino propanol and 2-aminopropanol and mixtures thereof. An embodiment of the invention is one, any or all of prior embodiments in this paragraph up through the first embodiment in this paragraph wherein the catalyst, UZM-54, is characterized by a zeolite having a microporous crystalline structure comprising a framework of $AlO_2$ and $SiO_2$ tetrahedral units, further including the element E and having the empirical composition in the as synthesized and anhydrous basis expressed by the empirical formula of $M_m^{n+}R_{1\ r1}^{p_1+}R_{2\ r2}^{p_2+}Al_{1-x}E_xSi_yO_z$ where "m" is the mole ratio of M to (Al+E) and varies from about 0 to about 1, "$r_1$" is the mole ratio of $R_1$ to (Al+E) and has a value of about 0.1 to about 3.0, "$r_2$" is the mole ratio of $R_2$ to (Al+E) and has a value of about 0 to about 3.0, E is an element selected from the group consisting of gallium, iron, boron, indium and mixtures thereof, "x" is the mole fraction of E and has a value from 0 to about 1.0, "y" is the mole ratio of Si to (Al+E) and varies from greater than 11 to about 30 and "z" is the mole ratio of O to (Al+E) and has a value determined by the equation $z=(m·n+r_1·p_1+r_2·p_2+3+4·y)/2$. An embodiment of the invention is one, any or all of prior embodiments in this paragraph up through the first embodiment in this paragraph further comprising passing the effluent stream to a para-xylene separation unit to generate a para-xylene process stream and a second stream comprising meta-xylene and ortho-xylene. An embodiment of the invention is one, any or all of prior embodiments in this paragraph up through the first embodiment in this paragraph wherein the separation unit is an adsorption separation unit and generates and extract stream comprising para-xylene and desorbent and a raffinate stream comprising meta-xylene and ortho-xylene. An embodiment of the invention is one, any or all of prior embodiments in this paragraph up through the first embodiment in this paragraph further comprising passing the extract stream to a fractionation unit to generate a bottoms stream comprising para-xylene and an overhead stream comprising desorbent. An embodiment of the invention is one, any or all of prior embodiments in this paragraph up through the first embodiment in this paragraph wherein the raffinate stream is passed to the isomerization reactor.

A second embodiment of the invention is a process for the production of para-xylene, comprising passing a mixture of hydrocarbons comprising xylenes to an isomerization reactor, operated at isomerization reaction conditions, to form a reaction mixture over an isomerization catalyst of the aluminosilicate zeolite UZM-54, and to generate an effluent stream comprising para-xylene, wherein the catalyst is a zeolite, UZM-54, of claim 1 having a microporous crystalline structure comprising a framework of $AlO_2$ and $SiO_2$ tetrahedral units, further including the element E and having the empirical composition in the as synthesized and anhydrous basis expressed by the empirical formula of $M_m^{n+}R_{1\ r1}^{p_1+}R_{2\ r2}^{p_2+}Al_{1-x}E_xSi_yO_z$ where "m" is the mole ratio of M to (Al+E) and varies from about 0 to about 1, "$r_1$" is the mole ratio of $R_1$ to (Al+E) and has a value of about 0.1 to about 3.0, "$r_2$" is the mole ratio of $R_2$ to (Al+E) and has a value of about 0 to about 3.0, E is an element selected from the group consisting of gallium, iron, boron, indium and mixtures thereof, "x" is the mole fraction of E and has a value from 0 to about 1.0, "y" is the mole ratio of Si to (Al+E) and varies from greater than 11 to about 30 and "z" is the mole ratio of O to (Al+E) and has a value determined by the equation $z=(m·n+r_1·p_1+r_2·p_2+3+4·y)/2$ and it is characterized in that it has the x-ray diffraction pattern having at least the d spacing and intensities set forth in the following Table:

TABLE

| 2Θ | d(Å) | I/Io |
|---|---|---|
| 7.91-8.05 | 10.83-11.16 | vs |
| 8.84-9.01 | 9.80-9.99 | vs |
| 14.87-14.91 | 5.93-5.95 | w-m |
| 15.51-15.65 | 5.65-5.70 | w |
| 15.91-16.12 | 5.49-5.56 | w |
| 20.41-20.59 | 4.31-4.34 | w |
| 20.82-20.94 | 4.25-4.43 | w |
| 23.25-23.61 | 3.76-3.82 | vs |
| 23.84-23.92 | 3.71-3.72 | m |
| 24.35-24.75 | 3.59-3.65 | m |
| 26.80-26.95 | 3.30-3.32 | w |
| 29.33-29.46 | 3.02-3.04 | w |
| 30.01-30.13 | 2.96-2.97 | w |
| 30.32-30.32 | 2.94-2.94 | w |

An embodiment of the invention is one, any or all of prior embodiments in this paragraph up through the second embodiment in this paragraph wherein the isomerization reaction conditions include a temperature between 190° C. and 350° C. An embodiment of the invention is one, any or all of prior embodiments in this paragraph up through the second embodiment in this paragraph wherein the isomerization reaction conditions include a pressure sufficient to maintain the reaction mixture in the liquid phase. An embodiment of the invention is one, any or all of prior embodiments in this paragraph up through the second embodiment in this paragraph wherein the pressure is at least 1025 kPa. An embodiment of the invention is one, any or all of prior embodiments in this paragraph up through the second embodiment in this paragraph wherein the mixture of hydrocarbons further includes ethylbenzene.

Other objects, advantages and applications of the present invention will become apparent to those skilled in the art from the following detailed description.

DETAILED DESCRIPTION

Para-xylene production is a valuable commercial process, wherein the reduction of losses can entail a significant economic advantage. One method of improving para-xylene yields is to increase the conversion from $C_8$ compounds to para-xylene and to reduce losses during that conversion. The operating of a liquid phase xylene isomerization reactor using a conventional MFI catalyst generates a significant xylene loss per pass. The loss is greater than 1.0%. The invention of a new catalyst, UZM-54, allows for a significant reduction in the xylene loss. The new catalyst has a new zeolitic MFI morphology, high meso-surface area and low Si/Al ratios and can achieve comparable para-xylene content with xylene losses of around 0.2% or less.

The present invention is a process for the production of para-xylene. The process includes passing a mixture of hydrocarbons including xylenes to an isomerization reactor, operated at isomerization reaction conditions to generate an effluent stream having para-xylene, or p-xylene. The reaction conditions include forming a reaction mixture comprising $C_7$-$C_9$ hydrocarbons and passing the mixture over an isomerization catalyst. The present invention utilizes a new catalyst that reduces the loss of xylenes during the isomerization process. The isomerization catalyst is a zeolite having a microporous crystalline structure comprising a framework of $AlO_2$ and $SiO_2$ tetrahedral units, and an empirical composition in the as synthesized and anhydrous basis expressed by the empirical formula of:

$$M_m^{n+}R_{1\ r1}^{p1+}R_{2\ r2}^{p2+}AlSi_yO_z.$$

The catalyst comprises M, which is at least one exchangeable cation selected from the group consisting of alkali and alkaline earth metals, "m" is the mole ratio of M to Al and varies from about 0 to about 1, $R_1$ is at least one organoammonium cation selected from the group consisting of quaternary ammonium cations, diquaternary ammonium cations, "$r_1$" is the mole ratio of $R_1$ to Al and has a value of about 0.1 to about 3.0, $R_2$ is at least one organoammonium cation selected from the group consisting of protonated alkanolamines, protonated amines, protonated diamines, and quaternized alkanolammonium cations, "$r_2$" is the mole ratio of $R_2$ to Al and has a value of about 0 to about 3.0, "n" is the weight average valence of M and has a value of about 1 to about 2, "$p_1$" is the weighted average valence of $R_1$ and has a value of about 1 to about 2, "$p_2$" is the weighted average valence of $R_2$ and has a value of about 1 to about 2, "y" is the mole ratio of Si to Al and varies from greater than 11 to about 30 and "z" is the mole ratio of O to Al and has a value determined by the equation:

$$z=(m \cdot n + r_1 \cdot p_1 + r_2 \cdot p_2 + 3 + 4 \cdot y)/2.$$

The catalyst, UZM-54, can be further characterized by its unique x-ray diffraction pattern as at least the d spacing and intensities set forth in Table A:

TABLE A

| 2Θ | d(Å) | I/Io |
|---|---|---|
| 7.91-8.05 | 10.83-11.16 | vs |
| 8.84-9.01 | 9.80-9.99 | vs |
| 14.87-14.91 | 5.93-5.95 | w-m |
| 15.51-15.65 | 5.65-5.70 | w |
| 15.91-16.12 | 5.49-5.56 | w |
| 20.41-20.59 | 4.31-4.34 | w |
| 20.82-20.94 | 4.25-4.43 | w |
| 23.25-23.61 | 3.76-3.82 | vs |
| 23.84-23.92 | 3.71-3.72 | m |
| 24.35-24.75 | 3.59-3.65 | m |
| 26.80-26.95 | 3.30-3.32 | w |
| 29.33-29.46 | 3.02-3.04 | w |
| 30.01-30.13 | 2.96-2.97 | w |
| 30.32-30.32 | 2.94-2.94 | w |

The M in the zeolite can be a mixture of alkali metals and alkaline earth metals, with a preferred M including one or more metals from lithium, sodium, potassium, cesium, strontium, calcium and barium. The $R_1$ cation can be selected from one or more of quaternary ammonium cations, quaternary phosphonium cations, and methonium cations. The $R_1$ cation can come from an halide compound or a hydroxide compound. Preferred $R_1$ cations include one or more from dimethyldipropylammonimum, diethyldipropylammonium, propyltrimethylammonium and hexamethonium. The R2 cation can come from an halide compound or a hydroxide compound. Preferred R2 cations include one or more from diethanolamine, N-methylethanolamine, 2-dimethylaminoethanol, N-methyldiethanolamine, 2-diethylamino ethanol, 2-isopropylamino ethanol, 2-diisopropylamino ethanol, 3-dimethylamino propanol and 2-aminopropanol.

The isomerization reaction conditions include a temperature between 190° C. and 350° C., with a preferred reaction temperature between 220° C. and 270° C. The reaction conditions include a pressure sufficient to maintain the reaction mixture in the liquid phase. In one embodiment, the pressure in the reactor is at least 1025 kPa, with a preferred reactor pressure in the range of 1750 kPa to 2400 kPa.

The feedstream preferably comprises $C_8$ aromatics, having para-xylene, meta-xylene and ortho-xylene. The feedstream can also include ethylbenzene, wherein the isomerization reactor converts the meta-xylene and ortho-xylene to para-xylene, and the ethylbenzene to benzene.

The effluent stream leaving the isomerization reactor includes para-xylene is passed to a para-xylene separation unit to generate a para-xylene process stream, and a second stream comprising meta-xylene, ortho-xylene and ethylbenzene. The para-xylene separation unit can comprise an adsorption separation unit, wherein the para-xylene process stream is the extract stream and the second stream is the raffinate stream. The extract stream and raffinate streams can include a desorbent. The extract stream is passed to a fractionation unit to generate a bottoms stream comprising para-xylene and an overhead stream comprising desorbent. The process can further include passing the raffinate stream to the isomerization reactor. The raffinate stream can also be passed to a second fractionation column to separate the desorbent from the raffinate stream before passing the raffinate stream to the isomerization reactor.

In another embodiment, the catalyst is characterized by a zeolite having a microporous crystalline structure comprising a framework of $AlO_2$ and $SiO_2$ tetrahedral units, further including the element E and having the empirical composition in the as synthesized and anhydrous basis expressed by the empirical formula of:

$$M_m^{n+}R_{1\ r1}^{p1+}R_{2\ r2}^{p2+}Al_{1-x}E_xSi_yO_z$$

where "m" is the mole ratio of M to (Al+E) and varies from about 0 to about 1, "$r_1$" is the mole ratio of $R_1$ to (Al+E) and has a value of about 0.1 to about 3.0, "$r_2$" is the mole ratio of $R_2$ to (Al+E) and has a value of about 0 to about 3.0, E is an element selected from the group consisting of gallium, iron, boron, indium and mixtures thereof, "x" is the mole fraction of E and has a value from 0 to about 1.0, "y" is the mole ratio of Si to (Al+E) and varies from greater than 11 to about 30 and "z" is the mole ratio of O to (Al+E) and has a value determined by the equation:

$$z=(m \cdot n + r_1 \cdot p_1 + r_2 \cdot p_2 + 3 + 4 \cdot y)/2.$$

Higher meso-surface area UZM-54 zeolite, show similar results for isomerization activity with respect to the paraxylene/xylene equilibrium, but has a much lower production of heavy components, or $C_{11+}$ aromatics, in the reactor. The high meso-surface area UZM-54 produces about 50% less heavier alkylated material in the effluent. Heavier alkylated material represents losses that are generally not recoverable in an aromatics complex.

EXAMPLE 1

An aluminosilicate reaction gel was prepared by first mixing 697.60 g of liquid sodium aluminate (LSA), 2178.08 g of dimethyldipropylammonimum hydroxide (40% SACHEM), 623.14 g of diethanolamine (Aldrich) and 14293.27 g of water while stirring vigorously. After thorough mixing, 3207.91 g of Ultrasil VN SP 89% was added. After the addition was completed, the resulting reaction mixture was homogenized for ½ hour, transferred to a 5-gallon hastelloy stir autoclave. The mixture was crystallized at 175° C. with stirring at 245 RPM for 92 hours. The solid product was recovered by centrifugation, washed with de-ionized water and dried at 80° C. The product was identified as UZM-54 by XRD. Representative diffraction lines observed for the product are shown in Table 1. The product composition was determined by elemental analysis to consist of the following mole ratios: Si/Al=13.45, Na/Al=0.0.589. A portion of the material was calcined by ramping to 600° C. for 2 hours followed by a 5 hour dwell in air. The BET surface area was 416 m$^2$/g, the micropore area was 229 m$^2$/g and the mesopore area was 187 m$^2$/g and the micropore volume was 0.118 cc/g and mesopore volume was 0.762 cc/g. Scanning Electron Microscopy (SEM) revealed crystals with a roughly spherical or rosette-like morphology of 10 to 25 nm. Chemical analysis was as follows: 3.07% Al, 42.9% Si, 1.54% Na, 0.90% N, N/Al=0.56, Na/Al=0.59 Si/Al$_2$=26.91.

TABLE 1

| 2θ | d(Å) | I/I$_0$ % |
|---|---|---|
| 7.91 | 11.16 | vs |
| 8.84 | 9.99 | vs |
| 14.87 | 5.95 | w |
| 15.91 | 5.56 | w |
| 23.26 | 3.82 | vs |
| 23.84 | 3.72 | m |
| 24.43 | 3.64 | m |
| 26.80 | 3.32 | w |
| 30.02 | 2.97 | w |
| 45.46 | 1.99 | w |

EXAMPLE 2

The pentasil zeolite of example 1 was formulated into a catalyst containing 70% zeolite and 30% silica. In the catalyst preparation, the zeolite was mixed with LUDOX AS-40 and Hi-Sil 250 into a Muller mixer. Additional water was added to the Muller mixer, while mixing, until dough with a proper texture for extrusion was formed. The dough was extruded to form 1/16" diameter trilobes, which were dried at 100° C. overnight and then sized to a length to diameter ratio of approximately 3. The dry extrudates was calcined in a box oven with a flowing air at 600° C. for 4 hours to remove the template. The calcined support was then exchanged using a 10 wt-% NH$_4$NO$_3$ solution at 75° C. for one hour. This was followed by water wash using 20 cc of water per cc of extrudates. The NH$_4$NO$_3$ exchange and water wash was repeated two more times. The extrudates was then dried at 120° C. for 4 hours and then activated at 550° C. The sodium level of the final catalyst was 0.003%. This is Catalyst A.

EXAMPLE 3

An aluminosilicate reaction gel was prepared by first mixing 697.60 g of liquid sodium aluminate (LSA), 2189.02 g of dimethyldipropylammonium hydroxide (39.8% SACHEM), 623.14 g of diethanolamine (Aldrich) and 14282.33 g of water while stirring vigorously. After thorough mixing, 3207.91 g of Ultrasil VN SP 89% was added. After the addition was completed, the resulting reaction mixture was homogenized for ½ hour, transferred to a 5-gallon hastelloy stir autoclave. The mixture was crystallized at 175° C. with stirring at 300 RPM for 89 hours. The solid product was recovered by centrifugation, washed with de-ionized water and dried at 80° C. The product was identified as UZM-54 by XRD. Representative diffraction lines observed for the product are shown in Table 2. The product composition was determined by elemental analysis to consist of the following mole ratios: Si/Al=13.92, Na/Al=0.59. A portion of the material was calcined by ramping to 600° C. for 2 hours followed by a 5 hour dwell in air. The BET surface area was 483 m$^2$/g, the micropore area was 197 m$^2$/g and the mesopore area was 286 m$^2$/g and the micropore volume was 0.101 cc/g and mesopore volume was 0.796 cc/g. Scanning Electron Microscopy (SEM) revealed crystals with a roughly spherical or rosette-like morphology of 10 to 25 nm. Chemical analysis was as follows: 2.98% Al, 43.1% Si, 1.50% Na, 0.93% N, N/Al=0.60, Na/Al=0.59, Si/Al$_2$=27.85.

TABLE 2

| 2θ | d(Å) | I/I$_0$ % |
|---|---|---|
| 7.97 | 11.08 | vs |
| 8.86 | 9.97 | s |
| 14.91 | 5.93 | w |
| 16.01 | 5.53 | w |
| 20.59 | 4.31 | w |
| 20.82 | 4.26 | w |
| 23.28 | 3.81 | vs |
| 23.86 | 3.72 | s |
| 24.51 | 3.62 | m |
| 26.95 | 3.30 | w |
| 29.33 | 3.04 | w |
| 30.13 | 2.96 | w |
| 45.13 | 2.00 | w |
| 45.43 | 1.99 | w |

EXAMPLE 4

The pentasil zeolite of example 3 was formulated into a catalyst containing 70% zeolite and 30% silica. In the catalyst preparation, the zeolite was mixed with LUDOX AS-40 and Hi-Sil 250 into a Muller mixer. Additional water was added to the Muller mixer, while mixing, until dough with a proper texture for extrusion was formed. The dough was extruded to form 1/16" diameter trilobes, which were dried at 100° C. overnight and then sized to a length to diameter ratio of approximately 3. The dry extrudates was calcined in a box oven with a flowing air at 600° C. for 4 hours to remove the template. The calcined support was then exchanged using a 10 wt-% NH$_4$NO$_3$ solution at 75° C. for one hour. This was followed by water wash using 20 cc of water per cc of extrudates. The NH$_4$NO$_3$ exchange and water wash was repeated two more times. The extrudates was then dried at 120° C. for 4 hours and then activated at 550° C. The sodium level of the final catalyst was 0.002%. This is Catalyst B.

EXAMPLE 5

Commercial MFI-23

Pentasil zeolite, purchased from Zeolyst International (lot: CBV 2314), was formulated into a catalyst containing 70% zeolite and 30% silica. In the catalyst preparation, the zeolite was mixed with LUDOX AS-40 and Hi-Sil 250 into a Muller mixer. Additional water was added to the Muller mixer, while mixing, until dough with a proper texture for extrusion was formed. The dough was extruded to form 1/16" diameter trilobes, which were dried at 100° C. overnight and then sized to a length to diameter ratio of approximately 3. The dry extrudates was calcined in a box oven with a flowing air at 600° C. for 4 hours to remove the template. The calcined support was then exchanged using a 10 wt-% NH$_4$NO$_3$ solution at 75° C. for one hour. This was followed by water wash using 20 cc of water per cc of extrudates. The NH$_4$NO$_3$ exchange and water wash was repeated three more times. The extrudates was then dried at 120° C. for 4 hours and then activated at 550° C. The sodium level of the final catalyst was 0.002%. This is Catalyst C.

EXAMPLE 6

Catalysts A-C were evaluated for xylene isomerization and ethyl-benzene retention using a pilot plant upflow reactor processing a non-equilibrium C$_8$ aromatic feed having the following approximate composition in wt-%:

| | |
|---|---|
| C$_{7-9}$ non-aromatics | 0.5 |
| ethylbenzene | 4.5 |
| para-xylene | 0.9 |
| meta-xylene | 64.6 |
| ortho-xylene | 29.5 |

EXAMPLE 7

Pilot-plant test conditions and results are as follows. The above feed contacted the Catalyst at a pressure of 3.5 MPa in the liquid phase at a weight hourly space velocity of 10 under a range of temperatures. The resulting performance measures are shown below:

| | Catalyst A | Catalyst B | Catalyst C |
|---|---|---|---|
| WHSV, hr −1 | 10 | 10 | 10 |
| Temperature to reach 23 PX/X, ° C. | 249 | 249 | 298 |
| Xylene Loss, wt % | 0.20 | 0.13 | 1.22 |
| A11+ selectivity, wt % | 0.07 | 0.04 | 0.11 |

Note that the "Xylene Loss" is in wt-% defined as "(1-(para, meta, ortho xylene wt % in product)/(-(para, meta, ortho xylene wt % in feed))*100", which represents material that has to be circulated to another unit in an aromatics complex. Such circulation is expensive and a low amount of C$_8$ ring loss is preferred. A11+ represents material that is heavier, and generally not recoverable.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:
1. A process for the production of para-xylene, comprising:
passing a mixture of hydrocarbons comprising xylenes to an isomerization reactor, operated at isomerization reaction conditions, to form a reaction mixture over an isomerization catalyst and to generate an effluent stream comprising para-xylene;
wherein the isomerization catalyst is characterized by a UZM-54 zeolite having a microporous crystalline structure comprising a framework of AlO$_2$ and SiO$_2$ tetrahedral units, and an empirical composition in the as synthesized and anhydrous basis expressed by the empirical formula of:

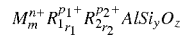

$$M^{n+}_m R1^{p1+}_{1r_1} R2^{p2+}_{2r_2} AlSi_yO_z$$

where M is at least one exchangeable cation selected from the group consisting of alkali and alkaline earth metals, "m" is the mole ratio of M to Al and varies from about 0 to about 1, R$_1$ is at least one organoammonium cation selected from the group consisting of quaternary ammonium cations and diquaternary ammonium cations, "r$_1$" is the mole ratio of R$_1$ to Al and has a value of about 0.1 to about 3.0, R$_2$ is at least one organoammonium cation selected from the group consisting of protonated alkanolamines, protonated amines, protonated diamines, and quaternized alkanolammonium cations, "r$_2$" is the mole ratio of R$_2$ to Al and has a value of about 0 to about 3.0, "n" is the weight average valence of M and has a value of about 1 to about 2, "p$_1$" is the weighted average valence of R$_1$ and has a value of about 1 to about 2, "p$_2$" is the weighted average valence of R$_2$ and has a value of about 1 to about 2, "y" is the mole ratio of Si to Al and varies from greater than 11 to about 30 and "z" is the mole ratio of O to Al and has a value determined by the equation:

$$z=(m \cdot n+r_1 \cdot p_1+r_2 \cdot p_2+3+4 \cdot y)/2$$

and it is characterized in that it has the x-ray diffraction pattern having at least the d spacing and intensities set forth in the following Table, wherein w=5.8-13.4, m=20.6-56.4, s=71.7-77.7, and vs=90.0-100.0:

| 2Θ | d(Å) | I/Io |
|---|---|---|
| 7.91-8.05 | 10.83-11.16 | vs |
| 8.84-9.01 | 9.80-9.99 | s |
| 14.87-14.91 | 5.93-5.95 | w |
| 15.91-16.12 | 5.49-5.56 | w |
| 20.41-20.59 | 4.31-4.34 | w |
| 20.82-20.94 | 4.25-4.43 | w |
| 23.25-23.61 | 3.76-3.82 | vs |
| 23.84-23.92 | 3.71-3.72 | m |
| 24.35-24.75 | 3.59-3.65 | m |
| 26.80-26.95 | 3.30-3.32 | w |
| 29.33-29.46 | 3.02-3.04 | w |
| 30.01-30.13 | 2.96-2.97 | w. |

2. The process of claim 1 wherein the isomerization reaction conditions include a temperature between 190° C. and 350° C.

3. The process of claim 2 wherein the isomerization reaction conditions include a temperature between 220° C. and 270° C.

4. The process of claim 1 wherein the isomerization reaction conditions include a pressure sufficient to maintain the reaction mixture in the liquid phase.

5. The process of claim 1 wherein the isomerization reaction conditions include a pressure of at least 1025 kPa.

6. The process of claim 1 wherein the mixture of hydrocarbons further includes ethylbenzene.

7. The process of claim 1 where M in the zeolite is selected from the group consisting of lithium, sodium, potassium, cesium, strontium, calcium, barium and mixtures thereof.

8. The process of claim 1 where M in the zeolite is a mixture of an alkali metal and an alkaline earth metal.

9. The process of claim 1 where $R_1$ in the zeolite is selected from the group consisting of dimethyldipropylammonium, diethyldipropylammonium, propyltrimethylammonium, and mixtures thereof.

10. The process of claim 1 where $R_2$ in the zeolite is selected from the group consisting of N-methylethanolamine, 2-dimethylaminoethanol, N-methyldiethanolamine, 2-diethylamino ethanol, 2-isopropylamino ethanol, 2-diisopropylamino ethanol, 3-dimethylamino propanol and 2-aminopropanol and mixtures thereof.

11. The processs of claim 1 wherein the catalyst is characterized by a zeolite having a microporous crystalline structure comprising a framework of $AlO_2$ and $SiO_2$ tetrahedral units, further including the element E and having the empirical composition in the as synthesized and anhydrous basis expressed by the empirical formula of:

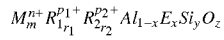

$$M_m^{n+}R1_{r_1}^{p1+}R2_{r_2}^{p2+}Al_{1-x}E_xSi_yO_z$$

where "m" is the mole ratio of M to (Al+E) and varies from about 0 to about 1, "$r_1$" is the mole ratio of $R_1$ to (Al+E) and has a value of about 0.1 to about 3.0, "$r_2$" is the mole ratio of $R_2$ to (Al+E) and has a value of about 0 to about 3.0, E is an element selected from the group consisting of gallium, iron, boron, indium and mixtures thereof, "x" is the mole fraction of E and has a value from 0 to about 1.0, "y" is the mole ratio of Si to (Al+E) and varies from greater than 11 to about 30 and "z" is the mole ratio of O to (Al+E) and has a value determined by the equation:

$$z=(m \cdot n+r_1 \cdot p_1+r_2 p_2+3+4y)/2.$$

12. The process of claim 1 further comprising:
passing the effluent stream to a para-xylene separation unit to generate a para-xylene process stream and a second stream comprising meta-xylene and ortho-xylene.

13. The process of claim 12 wherein the para-xylene separation unit is an adsorption separation unit and generates an extract stream comprising para-xylene and desorbent and a raffinate stream comprising meta-xylene and ortho-xylene.

14. The process of claim 13 further comprising passing the extract stream to a fractionation unit to generate a bottoms stream comprising para-xylene and an overhead stream comprising desorbent.

15. The process of claim 13 wherein the raffinate stream is passed to the isomerization reactor.

16. The process of claim 1 wherein a mesopores surface area of the UZM-54 zeolite is about 187 m²/g to about 286 m²/g.

17. The process of claim 1 wherein a mesopores volume of the UZM-54 zeolite is about 0.76 cc/g to about 0.8 cc/g.

18. A process for the production of para-xylene, comprising:
passing a mixture of hydrocarbons comprising xylenes to an isomerization reactor, operated at isomerization reaction conditions, to form a reaction mixture over an isomerization catalyst and to generate an effluent stream comprising para-xylene;
wherein the isomerization catalyst, wherein the catalyst is a zeolite having a microporous crystalline MFI structure comprising a framework of $AlO_2$ and $SiO_2$ tetrahedral units, further including the element E and having the empirical composition in the as synthesized and anhydrous basis expressed by the empirical formula of:

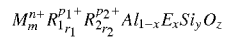

$$M_m^{n+}R1_{r_1}^{p1+}R2_{r_2}^{p2+}Al_{1-x}E_xSi_yO_z$$

where M is at least one exchangeable cation selected from the group consisting of alkali and alkaline earth metals, "m" is the mole ratio of M to (Al+E) and varies from about 0 to about 1, $R_1$ is at least one organoammonium cation selected from the group consisting of quaternary ammonium cations and diquaternary ammonium cations, "$r_1$" is the mole ratio of $R_1$ to (Al+E) and has a value of about 0.1 to about 3.0, $R_2$ is at least one organoammonium cation selected from the group consisting of protonated alkanolamines, protonated amines, protonated diamines, and quaternized alkanolammnoium cations, "$r_2$" is the mole ratio of $R_2$ to (Al+E) and has a value of about 0 to about 3.0, "n" is the weight average valence of M and has a value of about 1 to about 2, "$p_1$" is the weighted average valence of $R_1$ and has a value of about 1 to about 2, "$p_2$" is the weighted average valence of $R_2$ and has a value of about 1 to about 2, E is an element selected from the group consisting of gallium, iron, boron, indium and mixtures thereof, "x" is the mole fraction of E and has a value from 0 to about 1.0, "y" is the mole ratio of Si to (Al+E) and varies from greater than 11 to about 30 and "z" is the mole ratio of O to (Al+E) and has a value determined by the equation:

$$z=(m \cdot n+r_1 \cdot p_1+r_2 p_2+3+4y)/2$$

and it is characterized in that it has the x-ray diffraction pattern having at least the d spacing and intensities set forth in the following Table, wherein w=5.8-13.4 , m=20.6-56.4, s=71.7-77.7, and vs=90.0-100.0:

| 2Θ | d(Å) | I/Io |
|---|---|---|
| 7.91-8.05 | 10.83-11.16 | vs |
| 8.84-9.01 | 9.80-9.99 | s |
| 14.87-14.91 | 5.93-5.95 | w |
| 15.91-16.12 | 5.49-5.56 | w |
| 20.41-20.59 | 4.31-4.34 | w |
| 20.82-20.94 | 4.25-4.43 | w |
| 23.25-23.61 | 3.76-3.82 | vs |
| 23.84-23.92 | 3.71-3.72 | m |
| 24.35-24.75 | 3.59-3.65 | m |
| 26.80-26.95 | 3.30-3.32 | w |
| 29.33-29.46 | 3.02-3.04 | w |
| 30.01-30.13 | 2.96-2.97 | w. |

19. The process of claim 18 wherein the isomerization reaction conditions include a temperature between 190° C. and 350° C.

20. The process of claim 18 wherein the isomerization reaction conditions include a pressure sufficient to maintain the reaction mixture in the liquid phase.

21. The process of claim 18 wherein the isomerization reaction conditions include a pressure of at least 1025 kPa.

22. The process of claim 18 wherein the mixture of hydrocarbons further includes ethylbenzene.

* * * * *